United States Patent [19]

Tagata

[11] Patent Number: 4,857,731
[45] Date of Patent: Aug. 15, 1989

[54] INSTRUMENT FOR ANALYZING SPECIMEN

[75] Inventor: Shojiro Tagata, Tokyo, Japan

[73] Assignee: JEOL Ltd., Tokyo, Japan

[21] Appl. No.: 180,891

[22] Filed: Apr. 13, 1988

[30] Foreign Application Priority Data

Apr. 17, 1987 [JP] Japan .................................. 62-94715
Apr. 17, 1987 [JP] Japan .................................. 62-94716

[51] Int. Cl.⁴ ............................................. H01J 37/00
[52] U.S. Cl. ...................................... 250/310; 250/305
[58] Field of Search ................. 250/310, 305, 306, 307

[56] References Cited

U.S. PATENT DOCUMENTS

| | | | |
|---|---|---|---|
| 4,253,154 | 2/1981 | Russ et al. | 250/310 |
| 4,439,680 | 3/1984 | Broadhurst | 250/310 |
| 4,553,030 | 11/1985 | Tokiwai et al. | 250/307 |

OTHER PUBLICATIONS

"Microbeam Analysis 1985", John T. Armstrong, Ed., Proceedings of the 20th Annual Conference of the Microbeam Analysis Society, Louisville, Ky., 5–9 Aug. 1985, pp. 82–84, 145–147.

"Microbeam Analysis 1986", A. D. Romig, Jr. and W. F. Chambers, Eds., Proceedings of the 21st Annual Conference of the Microbeam Analysis Society, Albuquerque, New Mexico, 11–15 Aug. 1986, pp. 271–278.

Primary Examiner—Janice A. Howell
Assistant Examiner—Michael Aranoff
Attorney, Agent, or Firm—Webb, Burden, Ziesenheim, Webb

[57] ABSTRACT

An x-ray microanalyzer is a useful instrument which obtains an image representing the distribution of the constituent elements of a specimen, by detecting characteristic x-rays produced from a microscopic region on the specimen. The present invention is intended to enhance the efficiency of such an analysis of a specimen using an x-ray microanalyzer. A region of interest is designated upon the aforementioned image. The average weight concentration of the constituent elements in this region or information about the distribution of signal intensities is quickly obtained.

6 Claims, 3 Drawing Sheets

1

INSTRUMENT FOR ANALYZING SPECIMEN

FIELD OF THE INVENTION

The present invention relates to improvements in an x-ray microanalyzer or other similar instrument for investigating the distribution of chemical elements in a microscopic region on the surface of a specimen.

BACKGROUND OF THE INVENTION

In a specimen-analyzing instrument, such as an x-ray microanalyzer (or EPMA: Electron Probe X-ray Micro-Analyzer), a number of imaginary object elements are defined in a two-dimensional plane on the surface of a specimen. An electron beam is directed to these object elements successively. Characteristic x-rays are produced by chemical elements $\Theta_1, \eta_2, \ldots \Theta_n$ ($n \geq 2$) at the positions of the object elements (x, y), and the intensities of the x-rays are detected. Data about these intensities is stored in a memory, and then data regarding the intensities of the characteristic x-rays emanating from an arbitrary chemical element $\Theta_i$ is read from the memory, in accordance with the operator's instructions. Finally, the data read out in this way is sent to a display device or recorder.

When the instrument is so operated that the intensities of the characteristic x-rays derived from the certain chemical element $\Theta_i$ is digitized into n-state ($n \geq 2$) variables to obtain a color image on the principle of mapping, it is possible to roughly know the distribution of x-ray intensities. In providing such a color image, the signal indicating the intensities of x-rays is compared with plural reference levels to effect the aforementioned digitization. Then, different colors are assigned to values of different states, for creating a color image. Therefore, it is impossible to know the degree of homogeneity of the concentration of one element of interest within a region of the same color. That is, it is not possible to know whether the x-ray intensities at the object elements within this region lie in a wide or narrow range. The mapping techniques for obtaining color images are disclosed in "Microbeam Analysis 1985", p. 145–p. 147.

If it is possible to know the average weight concentration of an arbitrary chemical element $\Theta_j$ within a region of an arbitrary size at an arbitrary location on the viewing screen while a color image created by mapping is being observed, then more knowledge can be gained from this region. A known method of finding the weight concentration of an arbitrary chemical element is disclosed in "Microbeam Analysis 1985", p. 82–p. 84 and "Microbeam Analysis 1986", p. 271–p. 278.

SUMMARY OF THE INVENTION

It is a main object of the invention to provide a specimen-analyzing instrument which permits one to designate a region of an arbitrary size at an arbitrary position on a color coded image representing the distribution of the intensities of characteristic x-rays from object elements (locations) on a specimen and which can graphically display the frequency distribution of the intensities of characteristic x-rays produced from one chemical element over object elements corresponding to the picture elements contained in the designated region.

It is another object of the invention to provide a specimen-analyzing instrument which permits one to designate a region of an arbitrary region at an arbitrary position on a color coded image representing the distribution of the intensities of characteristic x-rays from object elements (locations) on a specimen and which can calculate and display the average weight concentration of an arbitrary chemical over object elements corresponding to the picture elements existing in the designated region.

These objects are achieved by an instrument for analyzing a specimen, said instrument having an analytical means for collecting data $I_1(x, y), I_2(x, y), \ldots, I_n(x, y)$ about the intensities of characteristic x-rays emanating from chemical elements $\Theta_1, \Theta_2, \ldots, \Theta_n$ ($n \geq 2$) and detected at object elements (x, y) defined in a two-dimensional plane on the specimen. A storage means stores the data collected by the analytical means. A display reads data $I_i(x, y)$ about the intensities of characteristic x-rays emanating from an arbitrary chemical element $\Theta_i$ (i is any one of 1, 2, ..., n) from the storage means. The display comprises a viewing screen defining picture elements displaying the data in a color code image representing the distribution of the chemical element $\Theta_i$. A designating means designates a region S of an arbitrary size at an arbitrary position on the viewing screen of the display means. The instrument is characterized by the provision of a means for displaying or drawing a chart representing the frequency distribution of the intensities of x-rays emanating from an arbitrary chemical element $\Theta_j$ (j is any one of 1, 2, ..., n) over said object elements corresponding to the picture elements contained at the region S or a means for displaying the results of the processings of the data collected from the region S.

DESCRIPTION OF THE PREFERRED EMBODIMENTS

Figure 1:
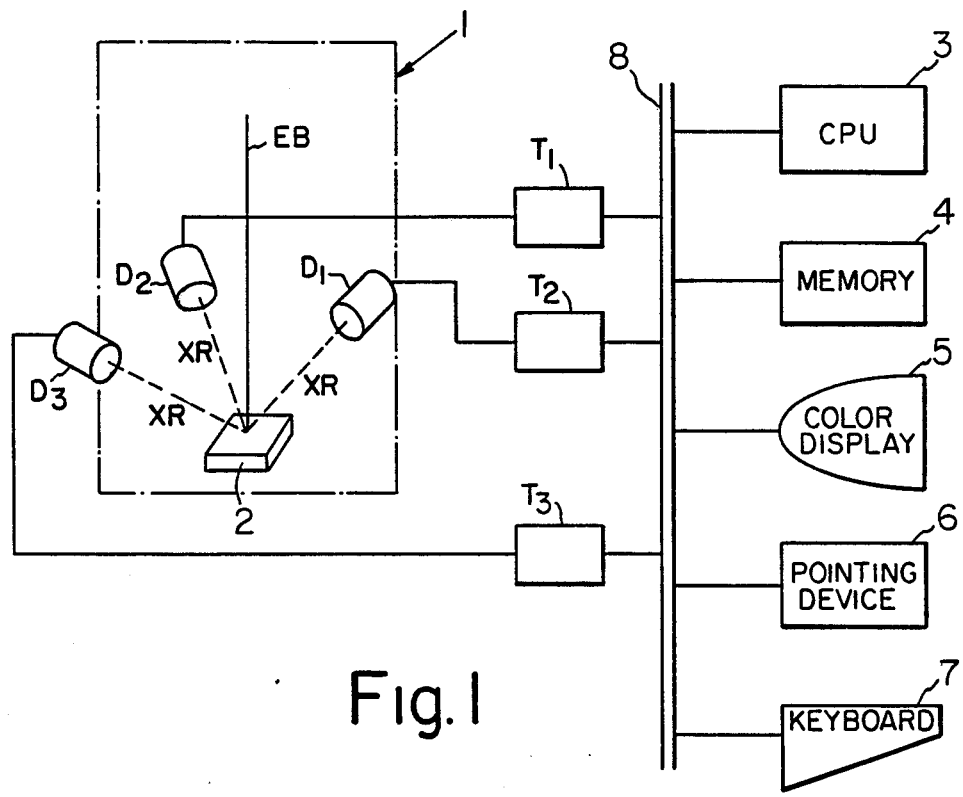
FIG. 1 is a schematic representation of an instrument according to the invention.

Referring to FIG. 1, a specimen 2 is placed in an x-ray microanalyzer 1. An electron beam EB is caused to strike the specimen 2, producing x-rays XR. X-ray spectrometers $D_1$, $D_2$, $D_3$ use diffracting crystals (not shown) to detect only certain wavelengths of x-rays. X-ray counters $T_1$, $T_2$, $T_3$ are connected with the spectrometers $D_1$, $D_2$, $D_3$, respectively. A CPU (central processing unit) 3, a memory 4, a color display 5, a digitizer or pointing device 6 such as a "mouse", and a keyboard 7 are connected with a bus 8. The x-ray spectrometers $D_1$, $D_2$, $D_3$ are designed to select characteristic x-rays emanating from elements $\Theta_1$, $\Theta_2$, $\Theta_3$, respectively. The pointing device 6 draws a region having an arbitrary size at an arbitrary location on the display 5 with the cursor according to the operator's instructions. Thus, the operator designates this region.

Figure 2:
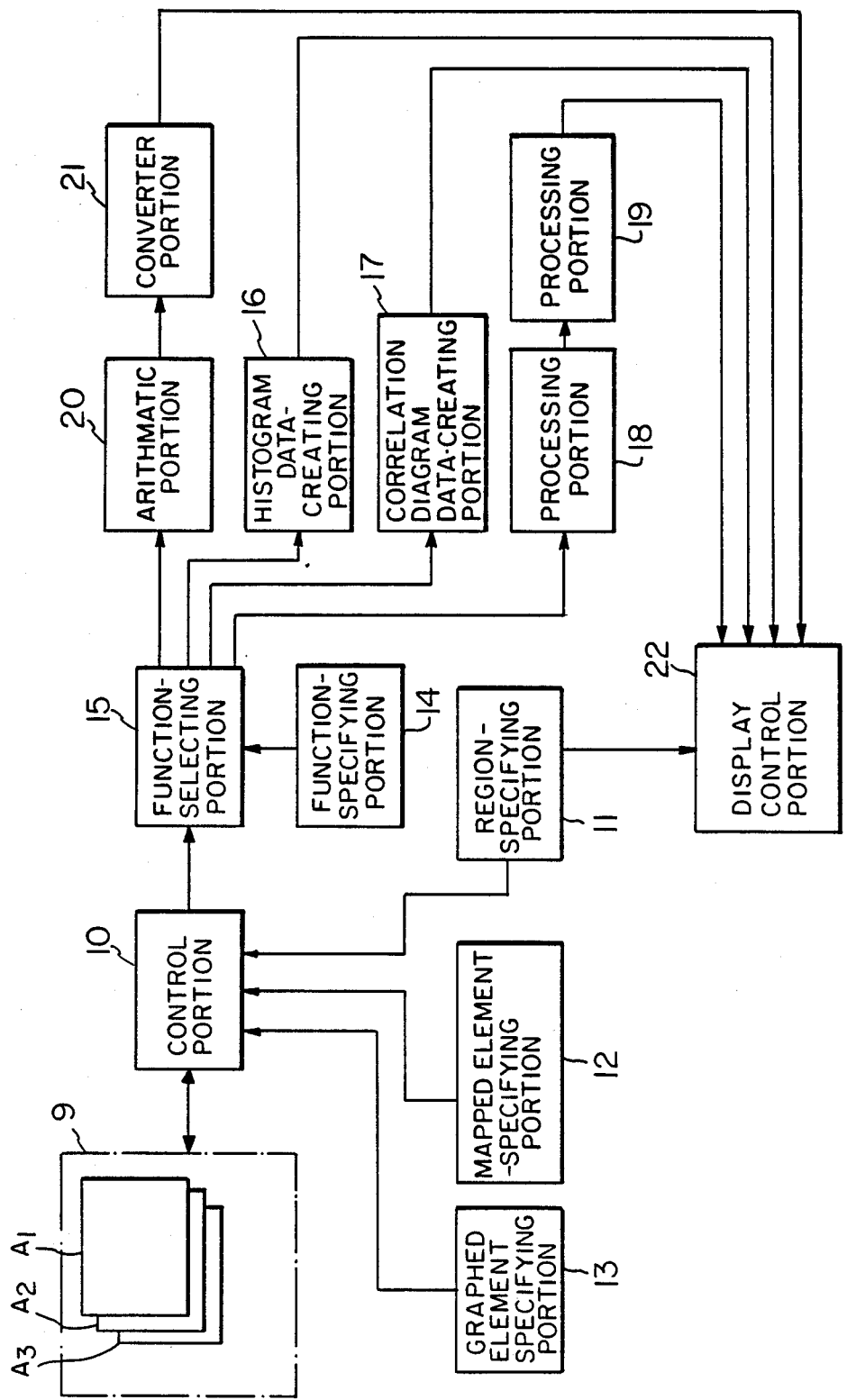
FIG. 2 is a block diagram of the instrument shown in FIG. 1.

FIG. 2 is a block diagram of the system shown in FIG. 1. The memory 4, shown in FIG. 1, has a storage area 9 for storing data about the intensities of x-rays, as shown in FIG. 2. The storage area 9 includes storage blocks $A_1$, $A_2$, $A_3$, each for storing data about one frame of image, corresponding to the elements $\Theta_1$, $\Theta_2$, $\Theta_3$, respectively. Each storage block has a given storage capacity to store data obtained from each picture element (x, y) which is scanned with the electron beam EB.

The system shown in FIG. 2 includes a control portion 10 for controlling reading and writing operations, a region-specifying portion 11, a mapped element-specifying portion 12, a graphed element-specifying portion 13 for specifying an element for which a histogram or correlation diagram (described later) is drawn, a function-specifying portion 14, a function-selecting portion 15, a histogram data-creating portion 16, a correlation diagram data-creating portion 17, a processing portion 18 for separation according to level, a processing portion 19 for color assignment, an arithmetic portion 20 for calculating average intensity, a converter portion 21 for obtaining concentration, and a display control portion 22. The specifying portions 11-14 are composed mainly of the keyboard 6 and programs stored in the memory 4 shown in FIG. 1. The display control portion 22 includes the color display 5 shown in FIG. 1.

The system constructed as described above operates in the manner described below. A mechanism (not shown) for horizontally moving the specimen 2 is driven to shift it along x- and y-axes while the specimen 2 is illuminated with the electron beam EB. As a result, the picture elements (x, y) on the specimen 2 are successively exposed to the beam EB. The specimen produces characteristic x-rays from the illuminated picture elements. Of the x-rays, the characteristic x-rays emanating from the elements $\Theta_1$, $\Theta_2$, $\Theta_3$ are detected by the x-ray spectrometers $D_1$, $D_2$, $D_3$, respectively. The output pulses from the spectrometers are counted by the x-ray counters $T_1$, $T_2$, $T_3$, respectively. The obtained total counts (or count rates) about the characteristic x-rays from the chemical elements $\Theta_1$, $\Theta_2$, $\Theta_3$ are sent to the memory 4 via the bus 8. Data about the element $\Theta_1$ is stored in the storage block $A_1$ of the storage area 9 corresponding to the picture elements (x, y). Similarly, data about the element $\theta_2$ is stored in the block $A_2$. Data concerning the element $\theta_3$ is stored in the block $A_3$.

Figure 3A:
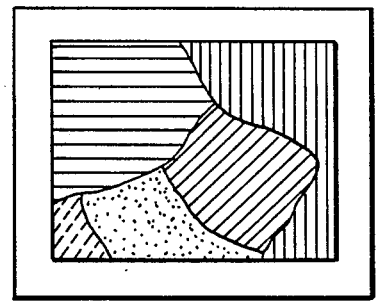
FIGS. 3(a)–3(d) and FIGS. 4(a) and 4(b) are diagrams for illustrating the operation of the instrument shown in FIG. 1.
Figure 3B:
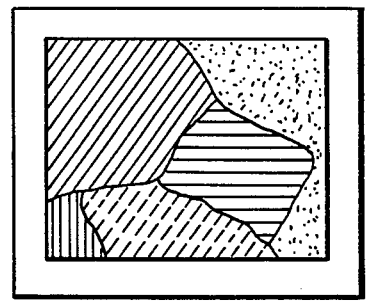

Under this condition, if the operator operates the keyboard 7 so as to provide a color display of the distribution of the characteristic x-rays emanating from the element $\Theta_1$, then the mapped element-specifying portion 12 causes the control portion 10 to select the element $\Theta_1$. The control portion 10 successively reads all that data stored in the storage block $A_1$ of the storage area 9, and sends it to the processing portion 18. This processing portion 18 then compares the incoming data with preset reference levels. The number and the values of the reference levels can be set at will. It is now assumed that the reference levels are four in number. The processing portion 18 divides every incoming data item into five classifications or ranges, according to these reference levels. The categorized data is fed to the processing portion 19, which then assigns hues to the input data according to the levels of the data. The output signal from the processing portion 19 is fed to the display control portion 22. As a result, a color mapping image as shown in FIG. 3(a) is displayed on the color display 5 to represent the distribution of the intensities of characteristic x-rays produced from the element $\theta_1$. Similarly, when the operator indicates display of an image representing the distribution of the intensities of characteristic x-rays emanating from the element $\Theta_2$, an image as shown in FIG. 3(b) is presented on the display 5, based on the data stored in the storage block $A_2$.

During the observation of the image representing the intensities of characteristic x-rays emanating from one element, for example $\Theta_2$, if the operator finds a region of interest and wants to have a histogram of the intensities of characteristic x-rays produced from the element $\Theta_2$ contained in this region, the following procedure is taken.

Figure 3C:
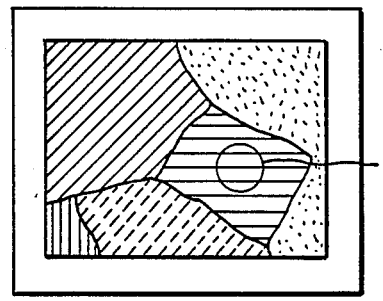
Figure 4A:
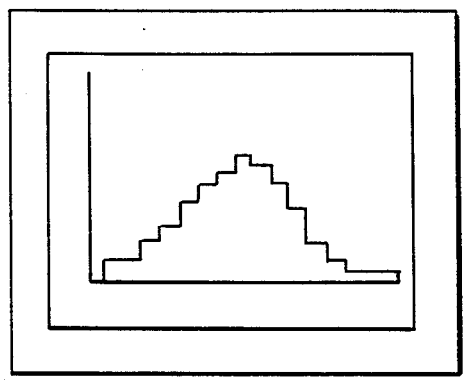

First, the operator operates the pointing device 6 to cause the region-specifying region 11 to surround this region $S_1$ with a bright line $F_1$ as shown in FIG. 3(c). After the completion of the designation of the region $S_1$, the operator operates the keyboard 7 to indicate that the element for which a histogram is displayed is $\Theta_2$. Then the element-specifying portion 13 signals the control portion 10 that data should be read from the storage block $A_2$. Further, the operator operates the keyboard 7 to indicate that graphical display provided on the display device takes the form of a histogram. The function-specifying portion 14 controls the function-selecting portion 15 in such a way that data sent out from the storage area 9 storing x-ray intensities is routed to the histogram data-creating portion 16. Thereafter, display of the histogram is ordered. Then, only the data concerning the picture elements contained in the region $S_1$ is read from the storage block $A_2$ of the storage area 9 by the control portion 10, in accordance with the output signal from the region-specifying portion 11. The data is supplied via the function-selecting portion 15 to the histogram data-creating portion 16, which distributes each incoming data item among a number of predetermined classes which are equally spaced from each other. For each class, the count is incremented on each data item assigned to the class. Thus, data representing the frequency distribution of x-ray intensities is created. The output signal from the histogram data-creating portion 16 is supplied to the display control portion 22, which then presents a histogram representing the frequency distribution of the x-ray intensities stemming from the element $\Theta_2$ as shown in FIG. 4(a). The operator who sees this display can gain knowledge of the degree of the homogeneity of the specimen. Specifically, if higher bars stand close together in the histogram, then the element $\Theta_2$ is distributed relatively uniformly over the region S1. If low bars stand widely, then the element $\Theta_2$ is distributed with less uniformity.

When the operator desires to present a histogram of the element $\Theta_1$, for example, it is only necessary to operate the keyboard 7 to indicate that the element is $\Theta_1$. Then, the element-specifying portion 13 signals the control portion 10 that data should be read from the storage block $A_1$. Data concerning the region $S_1$ is read from the storage block $A_1$ and processed to present a histogram of the element $\Theta_1$ on the display device 5.

Figure 4B:
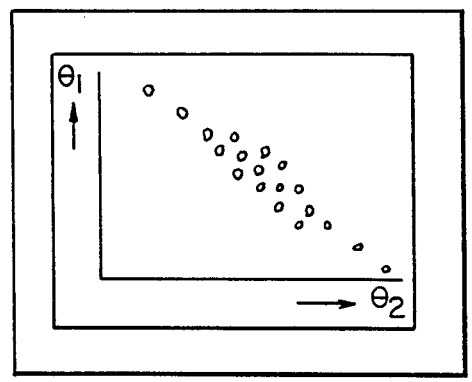

When the operator desires to know the distribution of intensities of x-rays produced by another element simultaneously and in a correlated manner with the distribution of intensities of x-rays originating from the aforementioned arbitrary element, he or she operates the keyboard 7 to execute display of a correlation diagram, as well as the designation of the region. Then, the function-specifying portion 14 supplies a control signal to the function-selecting portion 15 so that data is sent to the correlation diagram-creating portion 17 from the storage area 9. If the operator operates the keyboard 7 to display a correlation diagram of elements $\Theta_1$ and $\Theta_2$, for example, then the element-specifying portion 13 signals the control portion 10 that data should be read from the storage blocks $A_1$ and $A_2$. Subsequently, execution of the display is ordered. Data obtained from the picture elements contained in the region $S_1$ is transferred from the storage block $A_1$ to the correlation diagram data-creating portion 17 via the function selecting portion 15. Likewise, data derived from the picture elements contained in the region $S_1$ is sent from the storage block $A_2$ to the data-creating portion 17. The data-creating portion 17 processes its input data in such a way that the data stored in the block $A_1$ and arising from the i-th picture element contained in the region $S_1$ is taken as the x-coordinate $x_i$ of the i-th picture element displayed on the display device 5, and that the data stored in the block $A_2$ and derived from the i-th picture element contained in the region $S_1$ is taken as the y-coordinate of the i-th element. The data produced by these processings is sent to the display control portion 22 from the data-creating portion 17. Eventually, a correlation diagram as shown in FIG. 4(b) is presented on the display 5. The operator is able to see the degree of homogeneity of the distribution of each element from the displayed diagram. In particular, if the displayed dots are distributed widely along the axis of the element $\Theta_2$, it follows that the element $\Theta_2$ is distributed with low homogeneity. Conversely, if the dots are distributed within a narrow range along the axis of the element $\Theta_2$, then it can be said that the element $\Theta_2$ is uniform in concentration over the region $S_1$. Similarly, the spread of the dots along the axis of the element $\Theta_1$ shows the degree of homogeneity of the concentration of the element $\Theta_1$. In the illustrated example, the concentration of the element $\Theta_2$ has an inversely proportional relation to the concentration of the element $\Theta_1$ in the region $S_1$.

Figure 3D:
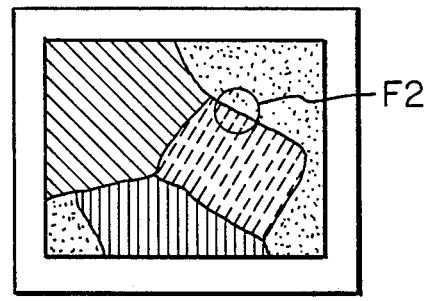

During observation of an image, as shown in FIG. 3(d), representing the distribution of the intensities of x-rays emanating from the element $\Theta_3$ on the color display 5, if the operator finds a region of interest and desires to know the average concentration of an arbitrary element in this region, he or she operates the pointing device 6 to cause the region-specifying portion 11 to encircle this region with a bright line $F_2$ as shown in FIG. 3(d). After the completion of the designation of the region, the keyboard 7 is operated to display the average weight concentration of the element $\Theta_3$, for example, in the specified region. Then, the element-specifying region 13 signals the control portion 10 that selected data should be read from the storage block $A_3$. At this time, the region-specifying portion 11 sends a signal indicating the specified region $S_2$ to the control portion 10. This control portion 10 then reads only data about the intensities of x-rays produced from the picture elements (x, y) contained in the region $S_2$ from the storage block $A_3$, and transmits it to the arithmetic portion 20. The arithmetic portion 20 calculates the average intensity of the x-rays produced by the element in the region $S_2$. The average intensity is given by $$M(\theta_3)_s = \frac{\int_s I(x, y) \, dx \cdot dy}{\int_s dx \cdot dy}$$

Thereafter, data indicative of the average intensity $M(\Theta_3)_s$ is fed to the converter portion 21 which converts its input data into data $W(\Theta_3)_s$ about the concentration of the element $\Theta_3$, using a calibration curve previously obtained employing a reference specimen. Instead of this method using a calibration curve, other quantitative analysis, such as the ZAF method or the B & A method can be utilized.

The data $W(\Theta_3)_s$ about the concentration is sent to the display control portion 22 from the converter portion 21. The control portion 22 displays the data $W(\Theta_3)_s$ in the form of characters on a lower portion or other portion of the viewing screen of the display 5 or causes a printer or the like to print the characters.

When the operator desires to know the average concentration of the element $\Theta_1$ in the region $S_2$, he or she operates the keyboard 7 to designate the element $\Theta_1$. Then, the element-specifying portion 13 supplies a signal specifying the element $\Theta_1$ to the control portion 10, which reads only data about the intensities of characteristic x-rays detected at the picture elements contained in the region $S_2$ from the storage block $A_1$. The data is fed to the arithmetic portion 12. Therefore, it is possible to display the average concentration of the element $\Theta_1$ existing in the region $S_2$ on the display device 5. Also, it is easy to compute and display the average concentrations of all the elements in the region $S_2$. Data about these elements are stored in the frame image storage blocks $A_1$, $A_2$, $A_3$, etc.

Figure 5:
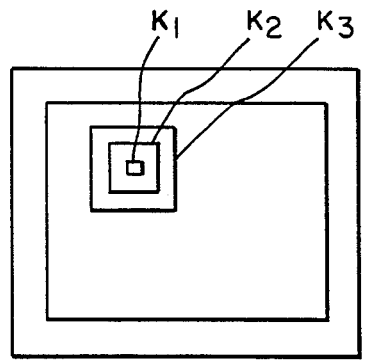
FIG. 5 is a schematic diagram for illustrating another instrument according to the invention.

It is to be understood that the foregoing relates to only one preferred embodiment of the invention and that the invention can be practiced otherwise than described above. In the above example, the pointing device is operated to designate a region which has an arbitrary shape, as well as arbitrary position and size. It is also possible to display a rectangle whose size can be changed in a stepwise fashion as indicated by $K_1$, $K_2$, $K_3$ in FIG. 5. The position of this rectangle can be also varied at will. The region may be specified by designating the position and the size of the rectangle.

Also in the above example, characteristic x-rays emitted by only three elements are detected, for simplicity. Characteristic x-rays emanating from more elements may be detected, and the obtained data may be stored in a memory. Further, the invention is applicable to an instrument making use of nondispersive x-ray spectrometers using semiconductor detectors instead of diffracting crystals to collect data about the intensities of characteristic x-rays emanating from elements. Furthermore, in the above example, data about the intensities of characteristic x-rays is used as it is to draw a histogram or correlation diagram. The data about the intensities may be converted into concentration values, using a calibration curve. Then, a histogram or correlation diagram may be displayed.

Having thus described my invention with the detail and particularity required by the Patent Laws, what is desired and claimed protected by Letters Patent is set forth in the following claims.

What is claimed is:

1. In an instrument for analyzing a specimen, said instrument having an analytical means for collecting data $I_1(x, y)$, $I_2(x, y)$, ..., $I_n(x, y)$ about the intensities of characteristic x-rays emanating from chemical elements $\Theta_1$, $\Theta_2$, ..., $\Theta_n$ ($n \geq 2$) at the positions of object elements (x, y) defined in a two-dimensional surface on the specimen, a storage means for storing the data collected by the analytical means, and a display means for reading data $I_i(x, y)$ about the intensities of characteristic x-rays emanating from an arbitrary chemical element $\Theta_i$ (i is any one of 1, 2, ..., n) from the storage means and said display means having a viewing screen defining picture elements for displaying the data in a color coded image representing the distribution of the chemical element $\Theta_i$ over the surface of the specimen, the improvement comprising:

a means for designating a region S on the viewing screen of the display means upon which is also displayed a color coded image of a selected chemical element $\Theta_i$ enabling selection of the stored data corresponding to a region on the surface of the specimen for further analysis; and means for drawing or displaying a chart representing the frequency distribution of the intensities of x-rays emanating from an arbitrary chemical $\Theta_j$ (j is any one of 1, 2, ..., n) over said object elements (x, y) corresponding to the picture elements contained in the region S.

2. In an instrument for analyzing a specimen, said instrument having an analytical means for collecting data $I_1(x, y)$ $I_2(x, y), ..., I_n(x, y)$ about the intensities of characteristic x-rays emanating from chemical elements $\Theta_1, \Theta_2, ..., \Theta_n$ ($n \geq 2$) at the positions of object elements (x, y) defined in a two-dimensional surface on the specimen, a storage means for storing the data collected by the analytical means, and a display means for reading data $I_i(x, y)$ about the intensities of characteristic x-rays emanating from an arbitrary chemical element $\Theta_i$ (i is any one of 1, 2, ..., n )from the storage means and said display means having a viewing screen defining picture elements for displaying the data in a color coded image representing the distribution of the chemical element $\Theta_i$ over the surface of the specimen, the improvement comprising:

a means for designating a region S on the viewing screen of the display means upon which is also displayed a color coded image of a selected chemical element $\Theta_i$ enabling selection of the stored data corresponding to a region on the surface of the specimen for further analysis; and a means for reading the intensities of x-rays emating from arbitrary two chemical elements $\Theta_j$ (j is any two of 1, 2, ..., n) of said object (x, y) elements corresponding to the picture elements contained in the region S and for drawing or displaying a chart that represents the correlation between these two elements.

3. In an instrument for analyzing a specimen, said instrument having an analytical means for collecting data $I_1(x, y), I_2(x, y), ..., I_n(x, y)$ about the intensities of characteristic x-rays emanating from chemical elements $\Theta_1, \Theta_2, ..., \Theta_n$ ($n \geq 2$) at the position of object elements (x, y) defined in a two-dimensional surface on the specimen, a storage means for storing the data collected by the analytical means, and a display means for reading data $I_i(x, y)$ about the intensities of characteristic x-rays from an arbitrary chemical element $\Theta_i$ (i is any one of 1, 2, ..., n) from the storage means and said display means having a viewing screen defining picture elements for displaying the data in a color coded image representing the distribution of the chemical element $\Theta_i$ over the surface of the specimen, the improvement comprising:

a means for designating a region S on the viewing screen of the display means upon which is also displayed a color coded image of a selected chemical element $\Theta_i$ enabling selection of the stored data corresponding to a region on the surface of the specimen for further analysis;

a means for finding the average value $M(j)_s$ of the intensities of characteristic x-rays emanating from an arbitrary chemical element $\Theta_j$ (j is any one of 1, 2, ..., n) over said object elements corresponding to the picture elements contained in the region S;

a means for converting the found average value $M(j)_s$ into a concentration $W(j)_s$ of the chemical element $\Theta_j$; and means for displaying the concentration $W(j)_s$.

4. In an instrument for analyzing a specimen, said instrument having an analytical means for collecting data $I_1(x, y), I_2(x, y), ..., I_n(x, y)$ about the intensities of characteristic x-rays emanating from chemical elements $\Theta_1, \Theta_2, ..., \Theta_n$ ($n \geq 2$) at the positions of object elements (x, y) defined in a two-dimensional surface on the specimen, a storage means for storing the data collected by the analytical means, and a display means for reading data $I_i(x, y)$ about the intensities of characteristic x-rays from an arbitrary chemical element $\Theta_i$ (i is any one of 1, 2, ..., n) from the storage means and said display means having a viewing screen defining picture elements for displaying the data in a color coded image representing the distribution of the chemical element $\Theta_i$ over the surface of the specimen, the improvement comprising:

means for designating a region S on the viewing screen of the display means upon which is also displayed a color coded image of a selected chemical element $\Theta_i$ enabling selection of the stored data corresponding to a region on the surface of the specimen for further analysis;

a means for finding the average value $M(j)_s$ of the intensities of characteristic x-rays emanating from a selected chemical element $\Theta_j$ (j is any of 1, 2, ..., n) over said object elements corresponding to the picture elements contained in the region S;

a means for converting the found average value $M(j)_s$ into a concentration $W(j)_s$ of the element $\Theta_j$; and a means for displaying the concentration $W(j)_s$.

5. In an instrument for analyzing a specimen, said instrument having an analytical means for collecting data $I_1(x, y), I_2(x, y), ..., I_n(x, y)$ about the intensities of characteristic x-rays emanating from a chemical elements $\Theta_1, \Theta_2, ..., \Theta_n$ ($n \geq 2$) at the positions of object elements (x, y) defined in a two-dimensional surface on the specimen, a storage means for storing the data collected by the analytical means, and a display means for reading data $I_i(x, y)$ about the intensities of characteristic x-rays from an arbitrary chemical element $\Theta_i$ (i is any one of 1, 2, ..., n) from the storage means and said display means having a viewing screen defining picture elements for displaying the data in a color coded image representing the distribution of the chemical element $\Theta_i$ over the surface of the specimen, the improvement comprising:

a means for designating a region S on the viewing screen of the display means upon which is also displayed a color coded image of a selected chemical element $\Theta_i$ enabling selection of the stored data corresponding to a region on the surface of the specimen for further analysis;

a means for finding the average value $M(j)_s$ of the intensities of characteristic x-rays emanating from a selected chemical element $\Theta_j$ (j is any one of 1, 2, ..., n) over said object elements corresponding to the picture elements contained in the region S;

a means for converting the found average value $M(j)_s$ into a concentration $W(j)_s$ of the chemical element $\Theta_j$;

a means for displaying the concentration $W(j)_s$; and a means for drawing or displaying a chart representing the frequency distribution of the intensities of x-rays emanating from a selected chemical element $\Theta_j$ (j is any one of 1, 2, ..., n) over said object elements (x, y) corresponding to the picture elements contained in the region S.

6. In an instrument for analyzing a specimen, said instrument having an analytical means for collecting data $I_1(x, y)$ $I_2(x, y)$, ..., $I_n(x, y)$ about the intensities of characteristic x-rays emanating from chemical elements $\Theta_1, \Theta_2, ..., \Theta_n$, (n≧2) at the positions of object elements (x, y) defined in a two-dimensional surface on the specimen, a storage means for storing the data collected by the analytical means, and a display means for reading data $I_i(x, y)$ about the intensities of characteristic x-rays from an arbitrary chemical element $\Theta_i$ (i is any one of 1, 2, ..., n) from the storage means and said display means having a viewing screen defining picture elements for displaying the data in a color coded image representing the distribution of the chemical element $\Theta_i$ over the surface of the specimen, the improvement comprising:

a means for designating a region S on the viewing screen of the display means upon which is also displayed a color coded image of a selected chemical element $\Theta_i$ enabling selection of the stored datas corresponding to a region on the surface of the specimen for further analysis;

a means for finding the average value $M(j)_s$ of the intensities of characteristic x-rays emanating from a selected chemical element $\Theta_j$ (j is any one of 1, 2, ..., n) over said object elements corresponding to the picture elements contained in the region S;

a means for converting the found average value $M(j)_s$ into a concentration $W(j)_s$ of the chemical element $\Theta_j$;

a means for displaying the concentration $W(j)_s$; and a means for reading the intensities of x-rays emanating from a selected two chemical elements $\Theta_j$ (j is any two of 1, 2, ..., n) of said object (x, y) elements corresponding to the picture elements contained in the region S and for drawing or displaying a chart that represents the correlation between these two elements.

* * * * *

UNITED STATES PATENT AND TRADEMARK OFFICE
CERTIFICATE OF CORRECTION

PATENT NO. : 4,857,731

DATED : August 15, 1989

INVENTOR(S) : Shojiro Tagata

It is certified that error appears in the above-identified patent and that said Letters Patent is hereby corrected as shown below:

Column 1 Line 17 "$n_2$" should read -- $\theta_2$ --.

Column 4 Line 44 "S1" should read -- $S_1$ --.

Claim 1 Line 12 Column 7 after "chemical" insert --element--.

Claim 2 Line 38 Column 7 "emating" should read --emanating--.

Claim 4 Line 35 Column 8 before "element" insert --chemical--.

Claim 5 Line 41 Column 8 before "chemical" delete --a--.

Claim 6 Line 10 Column 9 after "$I_1(x, y)$" insert --,--.

Claim 6 Line 12 Column 9 after "$\theta_n$" delete --,--.

Claim 6 Line 4 Column 10 "datas" should read --data--.

Claim 6 Line 17 Column 10 after "from" delete --a--.

Signed and Sealed this

Nineteenth Day of June, 1990

*Attest:*

HARRY F. MANBECK, JR.

*Attesting Officer*  *Commissioner of Patents and Trademarks*